United States Patent
Schlotterbeck Suárez et al.

(10) Patent No.: US 10,987,393 B2
(45) Date of Patent: Apr. 27, 2021

(54) **METHOD FOR PREVENTING AND CONTROLLING BACTERIAL INFECTIONS IN SALMONID FISH USING *QUILLAJA SAPONARIA* EXTRACTS**

(71) Applicant: SAPONIN RESEARCH CENTER S.A., Santiago de Chile (CL)

(72) Inventors: Trinidad Schlotterbeck Suárez, Santiago de Chile (CL); Hernán Alberto Cañon Jones, Santiago de Chile (CL); Mario Hernán Castillo Ruiz, Santiago de Chile (CL); Hernán Danilo Cortés González, Viña del Mar (CL); Ricardo Manuel San Martín Gamboa, Santiago de Chile (CL)

(73) Assignee: SAPONIN RESEARCH CENTER S.A., Santiago de Chile (CL)

( * ) Notice: Subject to any disclaimer, the term of this patent is extended or adjusted under 35 U.S.C. 154(b) by 23 days.

(21) Appl. No.: 16/527,849

(22) Filed: Jul. 31, 2019

(65) Prior Publication Data
US 2020/0023026 A1    Jan. 23, 2020

Related U.S. Application Data

(62) Division of application No. 15/543,977, filed as application No. PCT/CL2016/050044 on Jul. 29, 2016.

(51) Int. Cl.
| | |
|---|---|
| *A61K 36/185* | (2006.01) |
| *A23L 3/34* | (2006.01) |
| *A61K 36/73* | (2006.01) |
| *A23K 20/195* | (2016.01) |
| *A23K 50/80* | (2016.01) |

(Continued)

(52) U.S. Cl.
CPC .......... *A61K 36/185* (2013.01); *A23K 20/195* (2016.05); *A23K 50/80* (2016.05); *A23L 3/34* (2013.01); *A61K 9/0053* (2013.01); *A61K 36/73* (2013.01); *A61P 31/04* (2018.01)

(58) Field of Classification Search
CPC .................................................. A61K 36/185
See application file for complete search history.

(56) References Cited

U.S. PATENT DOCUMENTS

| | | |
|---|---|---|
| 2005/0074508 A1 | 4/2005 | San Martin |
| 2007/0196517 A1 | 8/2007 | San Martin |

FOREIGN PATENT DOCUMENTS

| | | |
|---|---|---|
| CL | 200402942 | 3/2006 |
| WO | 0151083 A2 | 7/2001 |

(Continued)

OTHER PUBLICATIONS

Fernandes, Rosangela Do Nascimento, (2014) Use of Quillaia saponin (*Quillaja saponaria molina*) in Juveniles of Pacu, Universidade Estadual Paulista, Faculty of Agricultural Sciences and Veterinary Center Aqüicultura, Brazil PhD Thesis Untranslated Jaboticabal, 2014 (115 pages).

(Continued)

*Primary Examiner* — Rosanne Kosson
(74) *Attorney, Agent, or Firm* — Procopio, Cory, Hargreaves & Savitch LLP

(57) ABSTRACT

The present invention discloses a new method for preventing and controlling bacterial diseases in salmonid fish using *Quillaja* extracts, wherein said method comprises administering to salmonid fish an effective amount of a medicinal composition comprising a *Quillaja saponaria* extract as active ingredient.

3 Claims, 1 Drawing Sheet

(51) Int. Cl.
*A61P 31/04* (2006.01)
*A61K 9/00* (2006.01)

(56) References Cited

FOREIGN PATENT DOCUMENTS

WO 2015155293 A1 10/2015
WO 2015179840 A1 11/2015

OTHER PUBLICATIONS

Vinay, Tharabenahalli-Nagaraju, et al. "Toxicity and Dose Determination of Quillaja Saponin, Aluminum Hydroxide and Squalene in Olive Flounder (*Paralichthys olivaceus*)" (2014), Veterinary immunology and immunopathology, 158 (1), Mar. 73-85, 2013 (14 pages).

Krogdahl, Ashild, et al. "Soya Saponins Induce Enteritis in Atlantic Salmon (*Salmo salar* L.)" Mar. 23, 2015, Journal of Agricultural and Food Chemistry 2015, 63, 3887-3902 (16 pages).

Henriquez, P., et al., "Comprehensive Antibiotic Susceptibility Profiling of Chilean Piscirickettsia samonis Field Isolates", Journal of Fish Diseases 2016, 39, 441-448 (2015) (8 pages).

Rozas, Marco, et al., "Piscirickettsiosis and Piscirickettsia salmonis in fish: A Review", Journal of Fish Diseases. (2013) (27 pages).

Pulgar, Rodrigo, et al., "Complete Genome Sequence of Piscirickettsia salmonis LF-89 (ATCC VR-1361) A Major Pathogen of Farmed Salmonid Fish" Journal of Biotechnology (2015) DOI: http://dx.doi.org/doi:10.1016/j.ibiotec.2015.07.017 (7 pages).

Tobar, Jaime A., et al., "Oral Vaccination of Atlantic Salmon (*Salmo salar*) Against Salmonid Rickettsial Septicaemia" Vaccine 29 (2011) 2336-2340) Mar. 2011, (7 pages).

Saez, Mora, et al, "Analisis de Antibiogramas de Cepas de Piscirichettsia salmonis Aisladas de Salmones y Truchas Cultivados en Las Regiones de los Rios, Los Lagos y Aysen Los Anos 2007 y 2008" 000196632 CDTV/UdeC/M79 2011 Universisdad de Concepcion, 2011. Downloaded Oct. 7, 2017 from http://cisne.bib.udec.cl/F/EQTNBMLGJF6BE7VCQ1G4DT7S7JM3BRLJ63CS1K3BUVLYG TI66V-51679?func=find-b&request=mora+piscirickettsi . . . (2 pages).

Tobar, Ivan, et al. "Successive Oral Immunizations against Piscirickettsia salmonis and Infectious Salmon Anemia Virus Are Required to Maintain a Long-Term Protection in Farmed Salmonids", May 27, 2015. Frontiers in Immunology, (6) 244, May 2015 (7 pages).

Kousoulaki, Katerina, et al. "Metabolism, Health and Fillet Nutritional Quality in Atlantic Salmon (*Salmo salar*) Fed Diets Containing n-3-rich Microalgae" (2015). Journal of Nutritional Science, vol. 4, c24, pp. 1-13 (13 pages).

San Martin, Ricardo and Briones, Reinaldo "Industrial Uses and Sustainable Supply of Quillaja Saponaria (Rosaceae) Saponins" (1999). Economic Botany, 53 (3), 302-311 (10 pages).

San Martin, Ricardo and Briones, Reinaldo "Quality Control of Commercial Quillaja (*Quillaja saponaria molina*) Extracts by Reverse Phase HPLC" (2000). Journal of the Science of Food and Agriculture, 80 (14), 2063-2068). (6 pages).

Maier, Christiane, et al. "Phenolic Constituents in Commercial Aqueous Quillaja (*Quillaja saponaria molina*) Wood Extracts" Journal of Agricultural and Food Chemistry, 63 (6), 1756-1762 (Jan. 27, 2015) (7 pages).

Elizondo, Ernesto A. Moya, et al. "Evaluation of a Quillaja Saponaria Saponin Extract for Control of Powdery Mildew of Wheat and Squash" (2010). Agro south, vol. 38 (2), 87-96 (10 pages).

Wang, Yujuan, et al., "Adjuvant Effect of Quillaja saponaria Saponin (QSS) on Protective Efficacy and IgM Generation in Turbot (*Scophthalmus maximus*) upon Immersion Vaccination" International Journal of Molecular Sciences, 2016, 17, 325 (13 pages).

METHOD FOR PREVENTING AND CONTROLLING BACTERIAL INFECTIONS IN SALMONID FISH USING *QUILLAJA SAPONARIA* EXTRACTS

CROSS-REFERENCE TO RELATED APPLICATIONS

This application is a Divisional Application of U.S. application Ser. No. 15/543,977, filed on Jul. 14, 2017, which U.S. National Stage entry of PCT Application No. PCT/CL2016/050044, filed on Jul. 29, 2016, the contents of which are incorporated herein by reference.

TECHNICAL FIELD

The present invention relates to the aquaculture industry, and particularly provides a new method for preventing and controlling bacterial diseases in salmonid fish using extracts of *Quillaja saponaria* trees.

BACKGROUND OF THE INVENTION

It is widely known that salmon farming industry has increased significantly worldwide in the last two decades and, particularly in Chile, this economic sector has become one of the most important in the country. However, there are different diseases caused by bacteria that infect fish and significantly affect the production.

Most of the bacterial diseases affecting salmonid fish are intracellular bacteria that share common strategies, like the Secretion Systems (TSS 1-7) to internalize, survive, replicate and stablish intracellular infections. For example, the main intracellular bacteria infecting fish in aquaculture are *Piscirickettsia salmonis, Renibacterium salmoninarum, Yersinia ruckeri, Edwardsiella tarda, Edwardsiella ictaruli, Francisella noatunensis* subsp. *Orientalis, Francisella noatunensis* subsp. *Noatunensis, Vibrio parahaemolyticus, Photobacterium damselae* subsp. *Piscicida, Candidatus piscichlamydia salmonis, Mycobacterium marinum, Mycobacterium chelonae, Mycobacterium gordonae, Mycobacterium fortuitum, Mycobacterium trivale, Candidatus pisciclamydia salmonis, Tasmanian Rickettsia*-like organism (RLO), and *Aeromonas salmonicida*.

Among bacterial diseases affecting fish, Piscirickettsiosis or septicemial rickettsial salmonid syndrome (SRS) caused by *Piscirickettsia salmonis*, is one of the most serious diseases that affects the salmon industry in Chile. Piscirickettsiosis affects fish during the seawater production cycle, causing high mortality rates that can reach 75% and economic losses for hundreds of millions of dollars (Henriquez, P., Kaiser, M., Bohle, H., Bustos, P., & Mancilla, M. (2016). Journal of fish Diseases 39 (4) 441-448).

To control Piscirickettsiosis, various strategies have been developed such as early harvesting of fish, the use of antibiotics and vaccines. Some factors that currently decrease the control of this pathogen are vaccines having limited efficacy and high quantities of antibiotics used in production, which may produce bacterial resistance to these drugs (Pulgar, R., Travisany, D., Zuniga, A. Maass, A., & Cambiazo, V. (2015). Journal of biotechnology, 212, 30-31). In addition, preventive actions involving the use of vaccines provide fish protection for short periods and are not effective in adult stages of salmon at the final stages of the production cycle (Tobar, J A, Jerez, S., Caruffo, M., Bravo, C., Contreras, F., Bucarey, S A, & Harel, M. (2011). Vaccine, 29 (12), 2336-2340). Moreover, it has been shown the existence of variants of *P. salmonis* resistant to the most commonly used antibiotics such as flumequine, enrofloxacin, erythromycin, amoxicillin and oxolinic acid (Mora, S J P, Farias, R C, Gadicke, L H P, Rozas, S M (2011). Thesis veterinary medicine: "Analysis of susceptibility of strains of *Piscirickettsia salmonis* isolated salmon and trout farmed in regions of the Rivers, Los Lagos and Aysen 2007 and 2008" University of Concepción, Faculty of veterinary Science). Due to the low efficacy of treatments and since the level of protection depends on various factors such as the immunobiology of fish, the conditions of administration of treatments and environmental factors, disease control has been difficult to achieve (Tobar, I. et al. (2015). Frontiers in immunology, (6) 244). Despite all the efforts, the high frequency of new epizootic events caused by *P. salmonis* indicate that there is a need for new alternatives to prevent and control this disease.

The most used bacterial vaccines in aquaculture have been based in inactivated bacteria (or killed wall cell bacteria), which evoke an antibody mediated response (humoral immune response) that can neutralize extracellular pathogens, but not intracellular pathogens. To destroy cells infected with intracellular pathogens is critical that the vaccine or other non-antibiotic alternatives induce the cellular immune response. This explain in part, why the current commercial vaccines, aimed to control Piscirickettsiosis (SRS) and other diseases caused by intracellular pathogens, that do not induce a cellular mediated immune response (CIR), have a low efficacy in their control. Therefore, there is a need for the development of vaccines and/or other non-antibiotic alternatives that evoke a cellular mediated immune response that can attack intracellular pathogens and eliminate infected cells (Munang'andu H M, Evensen Ø (2019). Fish Shellfish Immunol 85, 132-140).

One alternative to the use of vaccines and antibiotics for treating bacterial diseases in fish is administrating a food composition that allows the improvement of fish health. In this regard, various diets rich in microalgae containing polyunsaturated fatty acids, glycans, carotenoids, among others, have been tested. These ingredients can promote fish welfare while improving intestinal health and by increasing the resistance to diseases (Kousoulaki, K. et al. (2015). Journal of Nutritional Science, 4, e24).

*Quillaja saponaria* Molina (common name Quillay) is a native tree of Chile primarily used as a soap substitute due to the presence of saponins (San Martin, R. (1999). Economic Botany, 53 (3), 302-311). Saponins can be obtained industrially as powder or liquid extracts, and may be in a purified state, partially purified or unpurified. These extracts are marketed by several companies, being one of the most important Natural Response and Desert King (San Martin, R. and Briones, R. (2000). Journal of the Science of Food and Agriculture, 80 (14), 2063-2068).

To date, saponins rich extracts are used as natural emulsifiers in cosmetics, food and beverages. Additionally, these have been used as adjuvants for vaccine production and pharmaceutical formulations (Maier, C. et al. (2015). Journal of Agricultural and Food Chemistry, 63 (6), 1756-1762). Other uses such as biocide to eliminate nematodes (US 2005/0074508 A1), mollusks (US 2007/0196517 A1) and fungi (Moya Elizondo, E. A. et al. (2010). Agro Sur, 38 (2), 87-96) have also been described.

The review of Wang, Y. et al. (2016), International Journal of Molecular Sciences, 17 (3), 325, describes the use of saponins in aquatic animals showing that these can modulate the immune system of shrimp and fish, and also promote the growth of the latter. However, the document states that most saponins are unstable in aqueous conditions and are very toxic to fish at high concentrations.

Prior art analysis regarding the application of *Quillaja* extracts in fish, shows international patent application WO 2015/155293 A1 disclosing an oral food additive for use in the prevention and/or treatment of infections in a fish composition and particularly describes a composition comprising *Quillaja saponaria* saponins for prophylactic treatment against the ectoparasite of the genus *Caligus* in fish. The experimental evidence provided by this document does not include the determination of a beneficial effect against other pathogens such as bacteria and virus that affect salmonid fish.

International patent application WO 2015/179840 A1 describes combinations or compositions comprising *Yucca schidigera* and *Quillaja saponaria*, and further including antimicrobials, antibiotics and anticoccidial agents, for administration to animals to prevent diseases. As a general disclosure, it describes that they can be applied to fish orally.

International patent application WO 01/51083 A2 discloses an adjuvant composition comprising a saponin and an oligonucleotide comprising at least one CpG unmethylated dinucleotide. Preferably, the composition includes saponins derived from *Quillaja saponaria*, and most preferably, the saponin is chemically modified or substantially pure (QS7, QS17, QS18 or QS21). No description is done for the use in fish.

Chilean patent application CL 2942-2004 discloses a food additive for fish formulated with a purified extract of *Quillaja saponaria* Molina comprising 15-25% w/w of triterpene saponins obtained from said extract and 75-85% w/w of potato maltodextrin. This document discloses that the food additive improves the fish growth and feed conversion, but does not mention that this food additive could be effective against pathogens such as virus and bacteria that affect salmonid fish.

The PhD thesis of Fernandes, R. N, (2014) Using *Quillaja* saponin (*Quillaja saponaria* Molina) em juvenis of pacu, Universidade Estadual Paulista, Faculty of Agricultural Sciences and Veterinary Center Aqüicultura, Brazil, describes a study wherein the effect of administering *Quillaja* saponins in doses from 100 to 400 mg/kg in pacu fish (*Piaractus mesopotamicus*). After 15 days of feeding fish with *Quillaja* saponins, 325 fish were inoculated with *Aeromonas hydrophila* and clinical signs were observed. After seven days, the survival of pacu fish against experimental infection was higher in fish fed with *Quillaja* saponins in a dose of 200 mg/kg.

On the other hand, Vinay et al. (2014), Veterinary immunology and immunopathology, 158 (1), 73-85, describes an evaluation of the effect of *Quillaja* saponins administered intraperitoneally as vaccine adjuvant in *Paralichthys olivaceus*. This study showed that saponins are a good inducer of inflammation but are also toxic for the fish. Saponins concentrations of 500, 160, 50, 16 and 5 µg/fish produced 95%, 65%, 20% and 5% mortality rates, respectively, and with a lethal dose ($LD_{50}$) of 22.4 mg/kg. The results determined that the toxic effect of saponins depended on the level of purification and the source of the product. Finally, the authors found that a concentration of 3.4 mg/kg of fish is toxic when administered intraperitoneally, and it is recommended to use a lower concentration in *Paralichthys olivaceus*.

Regarding disclosures of saponins from sources other than *Quillaja saponaria*, Krogdahl et al. (2015), *Journal of Agricultural and Food Chemistry*, 63 (15), 3887-3902 discloses that soybean saponins administered orally as feed additive in doses of 2-10 g/kg produced intestinal inflammation in Atlantic salmon (*Salmo salar*), and the severity is dose-dependent.

This analysis of prior art shows that, although *Quillaja saponaria* saponins have been described for various uses and applications, they are used mainly as adjuvants and they are not associated with treatment of bacterial infections in commercial fish.

SUMMARY OF THE INVENTION

The present invention discloses a new method for controlling and preventing bacterial diseases in salmonid fish using *Quillaja* extracts, wherein said method comprises administering to salmonid fish an effective amount of a medicinal composition comprising a *Quillaja saponaria* extract as active ingredient and an appropriate excipient; wherein said *Quillaja saponaria* extract contains saponins.

Such medicinal preparation for salmonid fish is administered orally in a preferably dose range of 0.9 to 12 mg of saponins/kg live weight of fish per day. In a preferred embodiment, administration to salmonid fish is performed orally in combination with a food.

In a preferred embodiment, the bacterial disease is caused by a Gram-negative bacterium, wherein the bacteria are selected from the group consisting of *Piscirickettsia, Aeromonas* and *Vibrio*, and in a more preferred embodiment, the bacteria belonging to genus *Piscirickettsia* is *Piscirickettsia salmonis*.

In another preferred embodiment, the bacterial disease is caused by a Gram-positive bacterium, preferably bacteria belonging to the genus *Renibacterium*.

The present invention is intended for salmonid fish, preferably salmonid fish selected from the group consisting of *Salmo salar, Salmo trutta, Salmo gairdnerii, Oncorhynchus mykiss* or *Oncorhynchus kisutch* species.

DETAILED DESCRIPTION OF THE INVENTION

Figure 1:
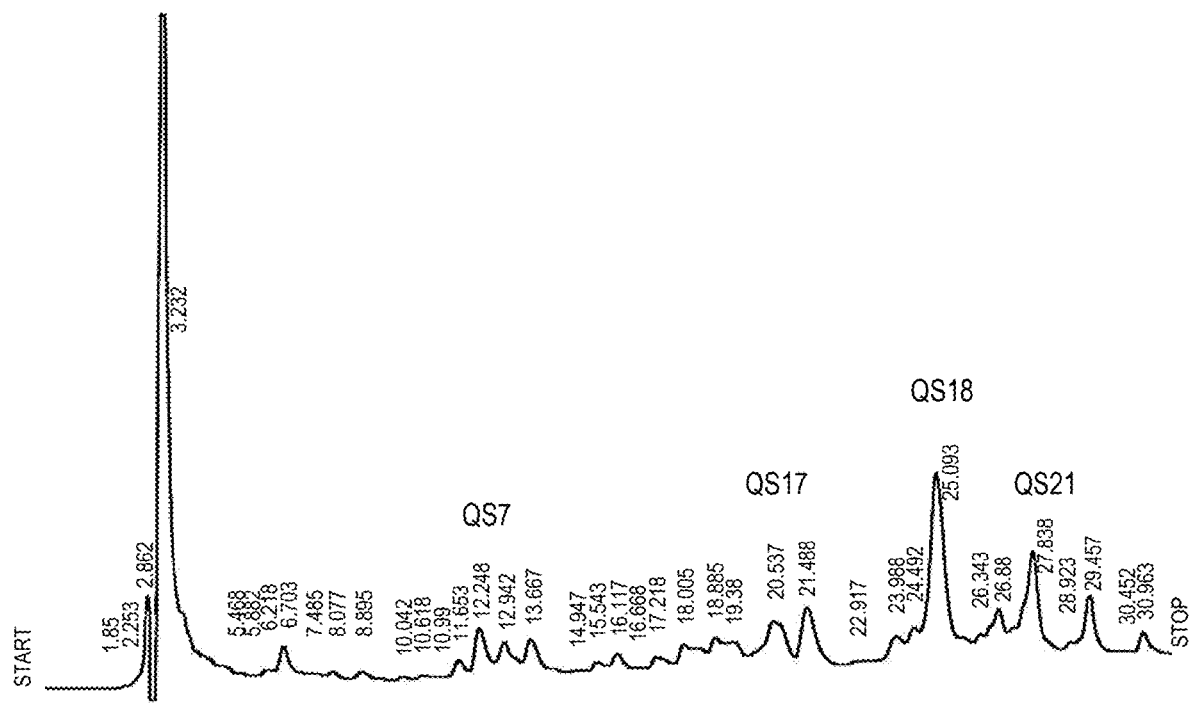
FIG. 1 is the chromatographic profile of a complete *Quillaja saponaria* Molina extract measured by HPLC, where the main saponins QS7, QS17, QS18 and QS21 are indicated.

The present invention describes a method for preventing and controlling bacterial infections that affect salmonid fish using plant extracts of *Quillaja saponaria*. Surprisingly, the inventors have found that different extracts of *Quillaja saponaria*, a Chilean endemic tree, particularly *Quillaja saponaria* Molina saponins, used as the only active ingredient in a medicinal composition have a protective effect against bacterial infections affecting salmonid farming, probably because said extracts induce a cellular mediated immune response needed to control intracellular pathogens infections like *Piscirickettsia salmonis* in aquaculture systems.

The inventors have tested and acquired appropriate dose concentrations of *Quillaja* extracts to be used safely in salmonid fish, without altering the physiopathology of treated individuals.

All technical and scientific terms used to describe the present invention have the same meaning understood by a person having a basic knowledge in this technical field. Notwithstanding, to define the scope of the invention more clearly, a list of terminology used in this description is included down below.

It should be understood that as used herein, the term "prevention" or "preventing" an infection refers to practical solutions designed to prevent the damages caused by infections (CDC's Infectious Disease. https://www.cdc.gov/ddid/framework.html). The prevention of disease in human and animals includes the implementation of the necessary practices to prevent the occurrence of a disease, but it does not imply that the disease does not occur. In fact, the actions that are taken to prevent a disease, including the use of vaccines, are aimed at increasing the "resistance" of patients (animals/humans) to this disease, i.e. the ability of the individual to moderate the cycle of life of the pathogen (its infectious cycle), which allows to reduce the transmission of the infection and therefore the severity of the disease at population level.

It should be understood that as used herein, the term "control" or "controlling" an infection refers to practical solutions that are applied to reduce the transmission of infections from one individual to another (Population Health Division, San Francisco Department of Public Health, Disease Prevention & Control. https://www.sfcdcp.org/communicable-disease/infection-control-practices/).

It should be understood that as used herein, the term "salmonid fish" refers to fish that belong to the Salmonidae family, which includes salmon, trout, chars, among others.

It should be understood that as used herein, the term "effective amount" refers to an amount of a compound, composition and/or formulation of the invention that is sufficient to produce a desired effect and is not toxic.

The present invention relates to a method for preventing and controlling bacterial infections in salmonid fish using effective amounts of a medicinal composition that comprises *Quillaja saponaria* extracts as the only active ingredient and an appropriate excipient; wherein said *Quillaja Saponaria* extract contains saponins.

The *Quillaja saponaria* extracts have a specific profile of saponins. In all cases, the profiles of these extracts are saponins own exclusive of *Quillaja saponaria*, as seen in the chromatographic profile of FIG. 1, either in purified extracts, partially purified or unpurified.

Entire or unfractionated extracts of preferably *Quillaja saponaria* Molina have a distinctive profile and own saponins containing over 100 types of chemically different saponins. *Quillaja* saponins are high molecular weight glycosides, containing a hydrophobic triterpenic nucleus and two hydrophilic sugar chains. The main saponins from this plant are QS7, QS17, QS18 and QS21 (Kensil C. R. (1991). J Immunol 146: 431-437), as seen in the chromatographic profile of FIG. 1.

The relative concentrations of these saponins depend on the source of the raw material that comes from the *Quillaja saponaria* tree, and also varies between the different species of trees. Additionally, the partially purified extracts (from 2 to 90% w/w or w/v of saponins depending on powder or liquid product) contain non-saponin compounds, which mainly include a mixture of polyphenols and, in smaller amounts, other sugars.

Extracts of *Quillaja* saponins can be obtained industrially as powder or liquid extracts, with varying degrees of purification. For example, for the purposes of the present invention various commercial extracts of *Quillaja saponaria* may be used, such as those shown in Table 1 below.

TABLE 1

Commercial extracts (Desert King Chile) of *Quillaja saponaria* useful for the present invention.

| Product name | Description |
| --- | --- |
| Ultra Dry ® 100-Q | *Quillaja saponaria* Molina powder extract, mainly containing triterpenoid saponins up to 65% w/w. |
| *Quillaja* Dry ® 100 | *Quillaja saponaria* Molina powder extract, mainly containing triterpenoid saponins up to 25% w/w. |
| Vax Sap ® | Highly purified *Quillaja saponaria* Molina powder extract mainly containing triterpenoid saponins >90% w/w. |
| QL 1000 ® | Liquid extract mainly of *Quillaja saponaria* Molina at a concentration of 8% w/v of triterpenoid saponins. |
| QL Perm ® | Liquid extract mainly of *Quillaja saponaria* Molina at a concentration of 2% w/v of triterpenoid saponins. |

The medicinal composition also includes appropriate excipients that may be any additive necessary for preparing said medicinal composition such as lactose, corn starch, silicon dioxide, binding agents, emulsions, surfactant, fatty acids, fats, oils, among others well known by experts of this area.

In a preferred embodiment of the present invention, the medicinal composition is administered to salmonid fish orally, in a liquid or solid form, but alternative methods of administration may be used such as immersion (bath treatments) or injections. Preferably, the medicinal composition is administered to the fish in combination with fish food. Said medicinal composition may be incorporated into the fish food during its production, for example, prior to pelleting, or may be incorporated into the fish food pellets, or granules impregnating them with the medicinal composition. Preferably, the *Quillaja saponaria* extracts are mixed with fish food in a pellet form, which is mixed with an equivalent to 2% of oil/weight of the pellet to impregnate, to adhere the extract to the food. Examples of fish diets widely known in the industry are produced by Ewos®, BioMar®, Salmofood®, Skretting®, among others. In a preferred embodiment, the food composition comprises food additives appropriate for oral administration in salmonids, such as fishmeal, fish and/or vegetable oil, vitamins, minerals, among others well known by experts of the area.

In a preferred embodiment, the medicinal composition is administered orally in a dose ranging from 0.9 to 12 mg saponins/kg of live weight of fish per day, but it may vary depending on the species of the salmonid fish treated. The medicinal composition could be administered to the salmonid fish in a single dose per day or could be equally divided in several doses per day, as long as the total dose required per day is administered. The medicinal composition could be administered through the entire productive cycle of fish from fry to adults, or could be administered in a specific time window, for example, only during months with higher probabilities of bacterial infection outbreak. For instance, in Chile, *Piscirickettsia salmonis* outbreaks are more likely to occur during the summer. The present invention encompasses the use of *Quillaja* extracts against bacteria that affect salmonid fish. Surprisingly, the administration of *Quillaja saponaria* extracts to salmonid fish is equally effective for preventing and controlling both Gram-negative bacteria and Gram-positive bacteria, probably due to its capacity to induce both Cellular Mediated Immunity (CMI), and a Humoral Mediated Immunity (HMI). CMI induced by *Quillaja saponaria* saponins eliminate infected cells, and HMI induced by *Quillaja saponaria* saponins induce the antibodies production that neutralize pathogens out of the cells.

The administration of *Quillaja saponaria* extracts to salmonid fish is effective preventing and controlling Gram-negative bacteria such as *Piscirickettsia salmonis, Aeromonas salmonicida* and *Vibrio* spp; and Gram-positive bacteria such as *Renibacterium salmoninarum*, or any other bacteria that affect the health of salmonid fish, either in freshwater or seawater. In a preferred embodiment, the method for preventing and controlling bacterial diseases is intended for bacterial diseases caused by *Piscirickettsia salmonis*. In another preferred embodiment, the method for preventing and controlling bacterial diseases is intended for bacterial diseases caused by *Renibacterium salmoninarum*.

The most susceptible species of salmonid fish are rainbow trout (*Oncorhynchus mykiss*), brook trout (*Salvelinus fontinalis*), brown trout (*Salmo trutta*), Arctic char (*Salvelinus alpinus*), Atlantic salmon (*Salmo salar*), Pacific salmon (*Oncorhynchus* spp.), chum salmon (*Oncorhynchus keta*), chinook salmon (*Oncorhynchus tshawytscha*), among others.

Examples have been included for the purpose of illustrating the invention, with the preferred embodiments and comparative examples, but in no case to be considered as a restriction to the scope of the patent application, which is only delimited by the content of the claims appended hereto.

EXAMPLES

Example 1

Evaluation of In Vitro and In Vivo Toxicity of *Quillaja* Extracts

In Vitro Citotoxicity Assay in Salmon Cell Lines.

Assays with *Quillaja* extracts products were tested on cell monolayers derived from salmon in order to assess the citotoxicity. The cell lines used were SHK-1 and ASK. SHK-1 line, described as macrophage-like cells (*Salmo salar*; ECACC 97111106 Number, European Collection of Cell Culture, Salisbury, Wilts, SP4 0JG, UK) was cultured at 15° C. in Leibovitz 15 medium (L-15, Gibco, Invitrogen, Carlsbad, Calif., USA) supplemented with 10% v/v fetal bovine serum (Hyclone, Thermo Fisher Scientific, Logan, Utah, USA), 4 mM L-glutamine (Gibco), 1% v/v 2-mercaptoethanol (2-ME, Gibco) and 50 µg/mL gentamicin (US Biological, Swampscott, Mass., USA). The cell line ASK (Atlantic Salmon Kidney, ATCC® CRL2747™) was cultured at 16° C. in Leibovitz (L-15, Hyclone, Thermo Scientific), supplemented with gentamicin (50 µg/mL), L-glutamine (4 mM) (Gibco, Thermo Scientific), 2-mercaptoethanol 1% (v/v) (2-ME, Gibco) and 10% fetal bovine serum (v/v) (FBS, Hyclone).

All *Quillaja* extracts products (Table 2) were prepared in MEM or 15 Leibovitz medium at a concentration of 1 mg/mL, being dissolved at 37° C. for 3 hours with gentle stirring. All prepared solutions of these extracts were filtered through a 0.22 µm nitrocellulose membrane to avoid contamination in cell cultures. The evaluated dilutions were prepared by serial dilutions from the standard solution.

To assess the cytotoxicity of *Quillaja* extracts in salmonid cell lines, $5 \times 10^5$ cells/well were seeded in 6-well plates and incubated in 2 mL of culture medium as final volume for 72 hours at 15° C. After this time the culture medium was replaced with fresh medium and the confluency was verified. After 24 hours, cells were incubated with the different *Quillaja* extracts in 1 mL of culture medium. Cytotoxicity assessment was made after 24 hours incubation with *Quillaja* extracts. For this, the cells were washed twice with cold PBS and then disrupted using a solution with 0.05% trypsin and 0.02% EDTA. Cells were analyzed by flow cytometry (FACS Canto II (Becton Dickinson) and cytosol incorporation of propidium iodide was determined as a marker for dead cells. Cells were incubated with a solution of ethanol as a positive control of cell death. As negative control, cells were incubated without *Quillaja* extracts, but were subjected to the same conditions. Additionally, cytotoxicity was assessed by visualizing cells by light microscopy.

Figure 2:
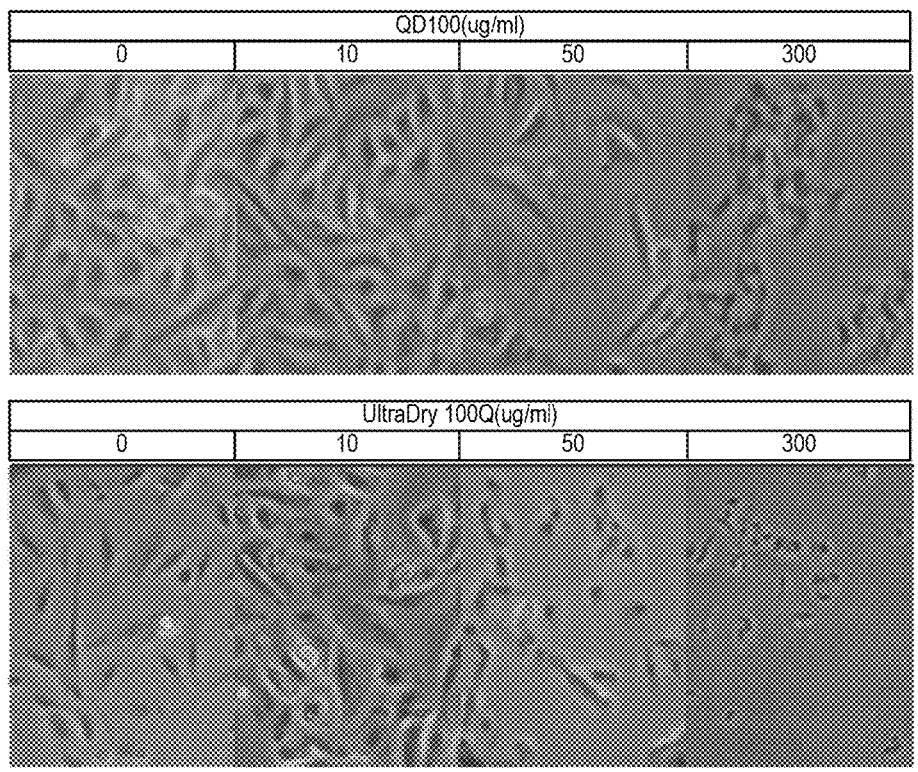
FIG. 2 is an image obtained by optical microscopy of an ASK salmonid cell line in the presence of different concentrations of *Quillaja* extracts UD100-Q (Ultra Dry® 100-Q) and QD100 (*Quillaja* Dry® 100).

Results indicated that the concentration that exhibited a 50% of cell death ($CC_{50}$) varied between 3.5 and 83.4 µg/mL and $CC_{90}$ varied between 4.7 and 92.6 µg/mL depending on the product used as indicated in Table 2. FIG. 2 shows representative results with products QD 100 (*Quillaja* Dry® 100) and UD 100Q (Ultra Dry® 100-Q) by viewing the cell monolayer through optical microscopy.

TABLE 2

Cell citotoxicity ($CC_{50}$) by flow citometry using propidium iodide.

| Product | $CC_{50}$ in SHK-1 (µg/mL) | $CC_{90}$ in SHK-1 (µg/mL) |
|---|---|---|
| Vax Sap ® | 20.4 | 25.3 |
| Ultra Dry ® 100-Q | 22.1 | 29.2 |
| *Quillaja* Dry ® 100 | 83.4 | 92.6 |
| QL 1000 ® | 3.7 | 6.5 |
| QL Perm ® | 3.5 | 4.7 |

In Vivo Oral Citotoxicity Assay in Fish.

To determine the short term oral toxicity (60 days) in fish, 550 Atlantic salmon (*Salmo salar*) fish clinically healthy were used, with an average weight of 9.5 g. Prior to the experiment, fish were acclimated for 8 weeks, during which 50 fish were randomly examined to check health condition through necropsy and microbiological tests to verify the absence of pathogens such as viruses, bacteria and parasites (Thoesen J. (1994) Suggested procedures for the detection and identification of finfish and shellfish Certain pathogens, 4$^{th}$ edn. Fish Health Section, *American Fisheries Society*, Bethesda, Md.; OIE (Office International des Epizooties) (2000) Diagnostic Manual for aquatic animal diseases, 3rd edn. OIE, Paris).

Fish were held in 1,000 L capacity fiberglass tanks, each with independent water supply. The level of dissolved oxygen in the water was 10 mg/L. Water temperature, and oxygen levels of nitrogen compounds were controlled daily.

Extruded feed pellets (Micro 10 prepared by Ewos®) were used to prepare five diets with 0, 100, 200, 300 and 600 ppm of saponins/kg of food (saponins from the commercial products Ultra Dry® 100-Q and *Quillaja* Dry® 100). These doses are equivalent to 0, 2, 4, 6 and 12 mg of saponins/kg of live weight of fish, respectively. Fish were divided into 10 individual tanks with 50 fish each (5 groups with duplicate).

Fishes were hand fed twice a day with diets according to the expected live weight and growth rate of fish. To do this the weight of fish where obtained at 0, 30 and 60 post-start of the experiment.

Fish were observed at least three times daily during the study, recording any possible clinical signs and mortalities. The experiment lasted 60 days. Results during the course of the trial showed no mortalities or abnormalities attributable to the product administered at the different doses. Additionally, no macro or microscopic pathological alterations in the liver or intestine in any treated group, compared to the control group, were found. In conclusion, administration of *Quillaja* extracts were safe at tested doses.

Example 2

Use of *Quillaja* Extracts for the Prevention and/or Treatment of In Vitro Bacterial Infection in Fish Antibacterial Activity of *Quillaja* Extracts Against *P. salmonis*.

The antibacterial activity of the extracts was measured through an infection assay in CHSE-214 cell monolayers derived from chinook salmon (*Oncorhynchus tshawytscha*, ATCC Number CRL-1681, American Type Culture Collection). $1.2 \times 10^6$ cells/well were seeded in 6-well plates and incubated at a confluence of 70%. To determine antibacterial activity, culture medium was removed and the cell monolayer was infected with a bacterial suspension of a Chilean *P. Salmonis* isolated with an approximate of $10^5$ genome copies/mL in culture medium (MEM, Hyclone) supplemented with HEPES buffer 10 mM (Hyclone), non-essential aminoacids (1×) (Hyclone) and 10% Fetal Bovine Serum (Hyclone). In addition, when was necessary the culture medium was supplemented with different *Quillaja* extracts, particularly Ultra Dry® 100-Q (UD100Q®, Desert King) (65% w/w of saponins) or *Quillaja* Dry® 100 (QD100®, Desert King) (25% w/w of saponins). Then, the capacity of *P. salmonis* infection was compared with the inoculum without *Quillaja* extracts.

The efficiency of the infection was quantified by qPCR through amplification of the 16S ribosomal gene. All conditions were done in triplicate. As a result, it was obtained that *Quillaja* extracts inhibited bacterial replication, where the product Ultra Dry® 100-Q managed to reduce replication by 97.98% when compared to the untreated control. *Quillaja* Dry® 100 product achieved a 64.40% inhibition of bacterial replication, as shown in Table 3 below.

TABLE 3

Results of infection inhibition of *Quillaja* extracts in CHSE-214 cells against *Piscirickettsia salmonis*.

| Treatment | Ct (dRn) | Copies/mL | Inhibitory concentration of total saponins (mg/mL) | Inhibition % |
|---|---|---|---|---|
| Control with bacteria | 15.29 | 7.94E+7 | 0 | 0 |
| UD100Q ® (65% of saponin purification) | 20.07 | 1.60E+6 | 0.00016 | 97.98 |
| QD100 ® (25% of saponin purification) | 14.73 | 1.94E+7 | 0.00053 | 64.40 |

Example 3

Preparation of a Fish Feed Impregnated with *Quillaja* Extracts

*Quillaja* extracts were mixed with fish oil to achieve the desired concentrations and then this mixture was impregnated at a rate of 4.9:1 (oil:dry pellet) in fish feed. This was done using an industrial mixer and incorporating oil in the food in movement for at least 5 minutes and additional mixing for at least 10 minutes.

To obtain a food composition impregnated with *Quillaja* extracts at the effective dose, important parameters to be considered are saponin doses/live weight of fish to be administered in the range from 0.9 to 12 mg of saponins per kilogram of live weight, fish weight and the amount of food they consume daily. The percentage of saponins in each particular *Quillaja* extract product should also be noted beforehand. Thus, any skilled person can obtain the ratio of saponins to be incorporated in the food.

As an example, to prepare a food composition considering the QL Perm® product, it must be used in a proportion of 6% w/w (60 g of product per kilogram of fish food).

Example 4

Use of *Quillaja* Extracts for the Prevention and/or Treatment of Fish Bacterial Infections In Vivo In Vivo Efficacy of *Quillaja* Products Against *Piscirickettsia salmonis*

One hundred and eighty Atlantic salmon (*Salmo salar*) weighting 30 g (fry) were used. Selected fishes had no history of ISAv and *P. salmonis* infection, which was checked by sampling and subsequent analysis of molecular diagnosis by RT-PCR in real time. Additionally, fishes were checked for bacterial and viral diseases. Before transferring to the experimental station, 60 fish were sampled for checking health status, which considered necropsy, gill inspection, intestine and skin sampling, Gram staining in internal organs (spleen, kidney and brain), staining with acridine orange in gills, IFAT analysis for BKD and SRS, and RT-PCR for IPNv. The general clinical appearance of the fish was acceptable and was within what is considered normal for the salmon industry and therefore representative of the Chilean fish industry.

During the test, fishes were fed with a diet of 15 micro EWOS 15CP® at a daily rate of 0.75% of body weight (bw/day) impregnated with a *Quillaja saponaria* extract (Ultra Dry® 100-Q o *Quillaja* Dry® 100, Desert King) in a dose of 3.75 mg product/kg of body weight.

The experiment was designed with the following experimental groups: positive control (fish challenged with the bacteria and fed without *Quillaja* extracts products), negative control (fish not challenged with bacteria and fed without *Quillaja* extracts products), and treatment groups (fish challenged with the bacteria and fed with *Quillaja* extracts products).

The challenge was performed using an experimental infection with *Piscirickettsia salmonis* by intraperitoneal injection in the ventral line at a rate of 0.1 mL of inoculum per fish, which had a title of $3 \times 10^6$ bacterial genome copies/mL. For the negative control group, fish were inoculated with 0.1 mL of culture medium. All experimental groups followed the following schedule, as indicated in Table 4 below.

TABLE 4

Time schedule for the in vivo efficacy study of *Quillaja* extracts for the prevention and/or control of piscirickettsiosis.

| Day | −15 | 0 | 1 | 7 | 45 |
|---|---|---|---|---|---|
| Acclimation | Start | Finish | | | |
| Treatment with orally given quillay extracts Ultra Dry ® 100-Q or *Quillaja* Dry ® 100 | | | Start | | Finish |
| Infection with *Piscirickettsia salmonis* | | | Start/Finish | | |
| Post-infection follow up | | | | Start | Finish |

TABLE 4-continued

Time schedule for the in vivo efficacy study of *Quillaja* extracts
for the prevention and/or control of piscirickettsiosis.

| Day | −15 | 0 | 1 | 7 | 45 |
|---|---|---|---|---|---|
| Post-treatment follow up | | | Start | | Finish |
| Assay time | Start | | | | Finish |

Results showed that Ultra Dry® 100-Q reduced mortality associated with infection of *Piscirickettsia salmonis* (SRS) by 37% when compared with the group challenged with the bacteria and fed with normal diet (without *Quillaja* extract). *Quillaja* Dry® 100 achieved a reduction of 18% compared to the same control, as shown in Table 5.

TABLE 5

Results of the in vivo study with functional
diets containing *Quillaja* extracts.

| Experimental groups | Mean mortality (%) | Mean survival (%) | Level of protection compared to controls (%) |
|---|---|---|---|
| Normal diet | 0 | 100 | — |
| Normal diet + infection with *Piscirickettsia salmonis* | 45.8 | 54.2 | — |
| Diet with UD100Q ® (66% saponin purity) + infection with *P. salmonis* | 29 | 71 | 36.68% |
| Diet with QD100 ® (26% saponin purity) + infection with *P. salmonis* | 37.5 | 62.5 | 18.12% |

Thus, results regarding the use of *Quillaja saponaria* extracts for the prevention and/or control of bacterial diseases in fish showed that these are highly effective, reflecting a protective effect against in vitro *Piscirickettsia salmonis* with efficacy over 60%; while in vivo a decrease in mortality associated to the bacterial infection was achieved between 18 to 36% at a concentration of 3.75 mg of product/kg live weight of fish using *Quillaja* extracts at different saponin purities.

The invention claimed is:

1. A method for controlling a bacterial disease caused by *Piscirickettsia salmonis* in *Salmo salar* fish, wherein said method comprises administering to *Salmo salar* fish an effective amount of a medicinal composition comprising a *Quillaja saponaria* extract as active ingredient and an appropriate excipient; wherein said *Quillaja saponaria* extract contains saponins.

2. The method according to claim 1, wherein the medicinal composition is administered to the fish orally in a dose ranging from 0.9 to 12 mg saponins/kg of live weight of fish per day.

3. The method according to claim 1, wherein the medicinal composition is administered to the fish in combination with fish food.

* * * * *